United States Patent [19]

Takahata

[11] Patent Number: 5,111,140
[45] Date of Patent: May 5, 1992

[54] APPARATUS AND METHOD FOR MEASURING REPULSIVE DISPLACEMENT AND REPULSIVE FORCE CHARACTERISTICS OF A SUPERCONDUCTOR WITH RESPECT TO A MAGNET

[75] Inventor: Ryoichi Takahata, Osaka, Japan

[73] Assignee: Koyo Seiko Co., Ltd., Osaka, Japan

[21] Appl. No.: 489,914

[22] Filed: Mar. 7, 1990

[30] Foreign Application Priority Data

Mar. 8, 1989 [JP] Japan .................................. 1-57442
Dec. 27, 1989 [JP] Japan .................................. 1-344767

[51] Int. Cl.$^5$ ...................... G01N 27/72; G01R 33/12
[52] U.S. Cl. .................................. 324/228; 324/226; 324/262; 505/842
[58] Field of Search ............... 324/226, 228, 234, 248, 324/262; 505/825, 842, 843

[56] References Cited

U.S. PATENT DOCUMENTS 4,939,458  7/1990  Yarar et al. ..................... 324/228
4,965,518  10/1990  Agarwala ........................ 324/228

Primary Examiner—Walter E. Snow
Attorney, Agent, or Firm—Finnegan, Henderson, Farabow, Garrett and Dunner

[57] ABSTRACT

Characteristics of a superconductor such as a repulsive displacement of a superconductor against a magnet or a rotational resistance of the superconductor due to flux-pinning in the superconductor are measured by supporting the superconductor in a non-contact mode; disposing a magnet at a position opposite to the superconductor; and moving the superconductor toward the magnet relatively or increasing the magnetic force of the magnet. The measurement may be carried out while the superconductor is applied with a load or is rotating.

16 Claims, 5 Drawing Sheets

APPARATUS AND METHOD FOR MEASURING REPULSIVE DISPLACEMENT AND REPULSIVE FORCE CHARACTERISTICS OF A SUPERCONDUCTOR WITH RESPECT TO A MAGNET

BACKGROUND OF THE INVENTION

The present invention relates to a device and a method for measuring characteristics of a superconductor such as repulsive displacements and repulsive forces with respect to a magnet.

A variety of mechanical components such as superconductor bearings, equipment and devices which utilize the repulsive force of a superconductor with respect to a magnet have been proposed in the art since high temperature superconductors were found. In actually designing and manufacturing such a mechanical component using the diamagnetism (the Meisner effect), it is necessary to quantitatively measure the repulsive displacement and repulsive force of the superconductor with respect to a magnet.

The following first and second methods for quantitatively measuring the repulsive force of a superconductor with respect to a magnet were published in Japan in the meeting of Cryogenic Engineering and Superconductor Society on Nov. 20, 1988. Further, the following third method was published in USA in Appl. Phys. Lett. 52(18), May 2, 1988, F. C. Moon et al.

In the first method, a superconductor specimen cooled lower than the critical temperature is levitated over a permanent magnet, and the height of the specimen is visually measured.

In the second method, a superconductor specimen suspended from a gravimeter is set over an electromagnet, and it is cooled by immersing it in liquid nitrogen. Under this condition, the levitation force of the superconductor specimen is measured by subtracting a weight of the specimen measured when an electric current is flown in the electromagnet from a weight of the specimen measured when no electric current is flown in the electromagnet, and also change of the levitation force in accordance with increase or decrease of the current flowing in the electromagnet is measured.

In the third method, the repulsive force is measured from the plastic deformation of a cantilever attached to a permanent magnet levitated over a superconductor.

In the above-described first method, the measurement is limited to a relatively short time, and is visually performed. Therefore, the results of measurement vary in accordance with the skill of the operators, that is, the results of measurement according to the first method have large errors and are low in reliability.

In the second method, it is necessary to measure the current flowing in the electromagnet and the weight of the superconductor specimen. This is relatively troublesome. In addition, the cooling liquid nitrogen permeates the superconductor specimen, as a result of which the measurement is lowered in accuracy.

Furthermore, in each of the above-described two methods, the measurement value includes the weight of the superconductor as a parameter. In order to obtain the repulsive displacement and repulsive force with respect to a magnet, it is necessary to measure the weight of the superconductor and to perform an arithmetic operation according to the weight thus measured. Thus, the measurement is rather troublesome, and low in accuracy.

In the third method, it is impossible to measure the effect of rotation of the superconductor.

By the way, superconductors are classified into two groups; a group of type I superconductor to which mainly pure metals belong, and a group of type II superconductor to which alloys, inorganic compounds, amorphous alloys and organic compounds belong.

A type I superconductor is perfect-diamagnetic and superconducting until the critical magnetic field is reached. A type II superconductor is perfect-diamagnetic until the lower critical magnetic field is reached, and it is not only superconducting but also normal-conducting when held between the lower critical magnetic field and the upper critical magnetic field; that is, in this state, it allows superconducting current while permitting a partial penetration of the magnetic field.

It has been known in the art that, when a type II superconductor is mixedly superconducting and normal-conducting, a kind of frictional force is induced by the magnetic flux passing through the superconductor. This is called "a suspension effect". For example, in the case where superconductor levitating over a magnet is mixedly superconducting and normal-conducting, even if the magnet is set above the superconductor, the superconductor will be held suspended in midair, and will not drop.

As was described above, with the type II superconductor which is mixedly superconducting and normal-conducting, a kind of frictional force is induced with the magnetic field. Hence, when such a superconductor is used for a mechanical part such as a bearing, then the frictional force would be a resistance against the operation of the mechanical part. Therefore, as for a type II superconductor, it is necessary to measure the range in which the superconductor is mixedly superconducting and normal-conducting, and the resistance provided when it is mixedly superconducting and normal-conducting.

For the type II superconductor, the fact that the superconductor is mixedly superconducting and normal-conducting under a predetermined condition and the suspension effect have been known as was described above; however, a method and apparatus for quantitatively measuring the range in which the superconductor is mixedly superconducting and normal-conducting (hereinafter referred to as "a mixedly superconducting and normal-conducting range", when applicable) and the mechanical resistance due to the magnetic flux pinning in the superconductor have not been proposed yet.

The state that the superconductor is mixedly superconducting and normal-conducting can be detected by measuring the susceptibility of a superconductor. However, the method cannot measure the repulsive displacement and repulsive force with respect to the magnet, or the mechanical force such as resistance due to the flux pinning in the superconductor.

Furthermore, the above-described three repulsive force measuring methods are merely able to measure the repulsive force of a superconductor with respect to a magnet. It goes without saying that the methods cannot measure the mixedly superconducting and normal-conducting range and the mechanical resistance due to the flux pinning in the superconductor.

SUMMARY OF THE INVENTION

In view of the foregoing, a first object of this invention is to make it possible to directly detect the repulsive displacement and repulsive force of a superconductor with respect to a magnet, thereby to measure the repulsive displacement and repulsive force with ease and to improve the measurement accuracy.

A second object of the invention is to make it possible to measure the above-described range in which a type II superconductor is mixedly superconducting and normal-conducting, the mechanical resistance provided when the superconductor is mixedly superconducting and normal-conducting, and the effect of rotation of the superconductor.

A third object of the invention is to make it possible for a single device to accurately measure the repulsive force against a magnet, and to measure characteristics concerning the mixedly superconducting and normal-conducting state, and to simplify the structure of the device by effectively using a gas for maintaining the superconductor at the critical temperature or lower.

The first object of the invention has been achieved by the provision of a superconductor characteristic measuring device, which, according to a first aspect of the invention, comprise: a specimen holding member for holding a superconductor specimen; supporting means for supporting the specimen holding member in a non-contact mode in such a manner that the specimen holding member is movable in a horizontal direction; a magnet positioned in such a manner as to confront, in the horizontal direction, with the superconductor specimen held by the specimen holding member; and displacement detecting means for detecting, in a non-contact mode, an amount of displacement of the specimen holding member in a horizontal direction.

The non-contact type supporting means may be one using gas such as a gas bearing, or one using the repulsive force or attractive force between magnets. In the latter case, magnetic shielding means is provided between the superconductor specimen and the supporting means so that the magnetic force of the supporting means may not affect the superconductor specimen. The magnet confronting with the superconductor specimen may be an electromagnet or a permanent magnet. The non-contact type displacement detecting means may be one which is so designed as to optically detect the displacement, or one which is so designed as to detect the displacement from variation of the magnetic field. The superconductor specimen may be maintained at the critical temperature or less by placing the whole device in a cooling chamber, or by utilizing the specimen holding member or the ambient atmosphere.

The second object of the invention has been achieved by the provision of a superconductor characteristic measuring device, which, according to a second aspect of the invention, comprises: a specimen holding shaft for holding a superconductor specimen; a magnet positioned in such a manner as to confront with the superconductor specimen held by the specimen holding shaft; supporting means for supporting the specimen holding shaft in such a manner that the specimen holding shaft is rotatably and movable towards and away from the magnet; rotation driving means for rotating the superconductor specimen; and rotational resistance detecting means for detecting a rotational resistance of the superconductor specimen.

In the measuring device, the magnet may be a permanent magnet or an electromagnet. It is not always necessary that the supporting means supports the specimen holding shaft in a non-contact mode; that is, it may be one which can support the specimen holding shaft with less resistance. The magnet and the supporting means are provided in a horizontal plane. However, the specimen holding shaft may be suspended above the magnet by using spring means. The rotation driving means and the rotational resistance detecting means may be held in contact with the specimen holding shaft or superconductor specimen. The superconductor specimen may be cooled down to the critical temperature or lower by placing the whole measuring device in a cooling chamber, or by utilizing the specimen holding shaft or the ambient atmosphere.

The third object of the invention has been achieved by the provision of a superconductor characteristic measuring device, which, according to a third aspect of the invention, comprises: a specimen holding shaft for holding a superconductor specimen; a gas bearing for supporting the specimen holding shaft in such a manner that the specimen holding shaft is held horizontal and is rotatably and axially movable; gas drive means for jetting a gas to a turbine section provided on the specimen holding shaft, to rotate the specimen holding shaft; gas supplying means for supplying a temperature maintaining gas to the gas drive means and the gas bearing; an electromagnet positioned in such a manner as to confront with the specimen in a horizontal direction; displacement detecting means for detecting an amount of axial displacement of the specimen holding shaft in a non-contact mode; and rotational resistance detecting means for detecting a rotational resistance of the superconductor specimen.

In the case where, in the measuring device according to the first aspect of the invention, the magnet is an electromagnet, the measurement is carried out as follows: The superconductor specimen is brought into contact with the electromagnet, the field strength of which is set to zero (at a standard position). Under this condition, the current flowing in the electromagnet is gradually increased, and the amount of displacement from said standard position of the specimen holding shaft is detected by the displacement detecting means. In the case where, on the other hand, the magnet is a permanent magnet, the permanent magnet is gradually moved towards the superconductor specimen. Further, the amount of displacement of the superconductor specimen from a predetermined position (standard position) due to the repulsive force to the speciment against a magnetic field generating means may be measured by keeping the magnetic field strength of the magnetic field generating means at some value, moving the superconductor specimen toward the magnetic field generating means by applying a load to the specimen in the horizxontal direction so as to stop the specimen at the predetermined position (standard position) while some magnetic flux passes through the specimen, and then removing the load from the specimen at the position. As the superconductor specimen and the specimen holding member are supported by the supporting means, their weight will not affect the repulsive displacement. Accordingly, the repulsive displacement of the superconductor specimen against the magnet is directly measured by the displacement detecting means.

In the measuring device according to the second aspect of the invention, the specimen holding shaft and the superconductor specimen are forcibly rotated by the rotating means, and the resistance acting on the superconductor specimen is measured by the rotational resistance measuring means, whereby it is determined whether or not the superconductor specimen is mixedly superconducting and normal-conducting, and the range in which the superconductor specimen is mixedly superconducting and normal-conducting, and the mechanical resistance when it is in that state, can be measured. Of course, the strength of the repulsive force itself of the superconductor specimen against the magnet at the time of rotation can be measured.

In the measuring device according to the third aspect of the invention, by inclining the measuring device, the displacement detecting means can measure the repulsive displacement under any load. Furthermore, the range in which the superconductor specimen is mixedly superconducting and normal-conducting, and the mechanical resistance given when it is in that state can be measured by rotating the superconductor specimen together with the specimen holding shaft. In addition, the repulsive displacement and the repulsive force at the time of rotation can be measured. Since the gas supplied to the gas bearing and the gas drive means cools down the specimen holding shaft and the superconductor specimen, the specimen-holding-shaft supporting means, the rotation driving means, and the cooling means can be simplified in construction as much.

DETAILED DESCRIPTION OF THE INVENTION

The preferred embodiments of the present invention will be described in detail with reference to the accompanying drawings.

Figure 1:
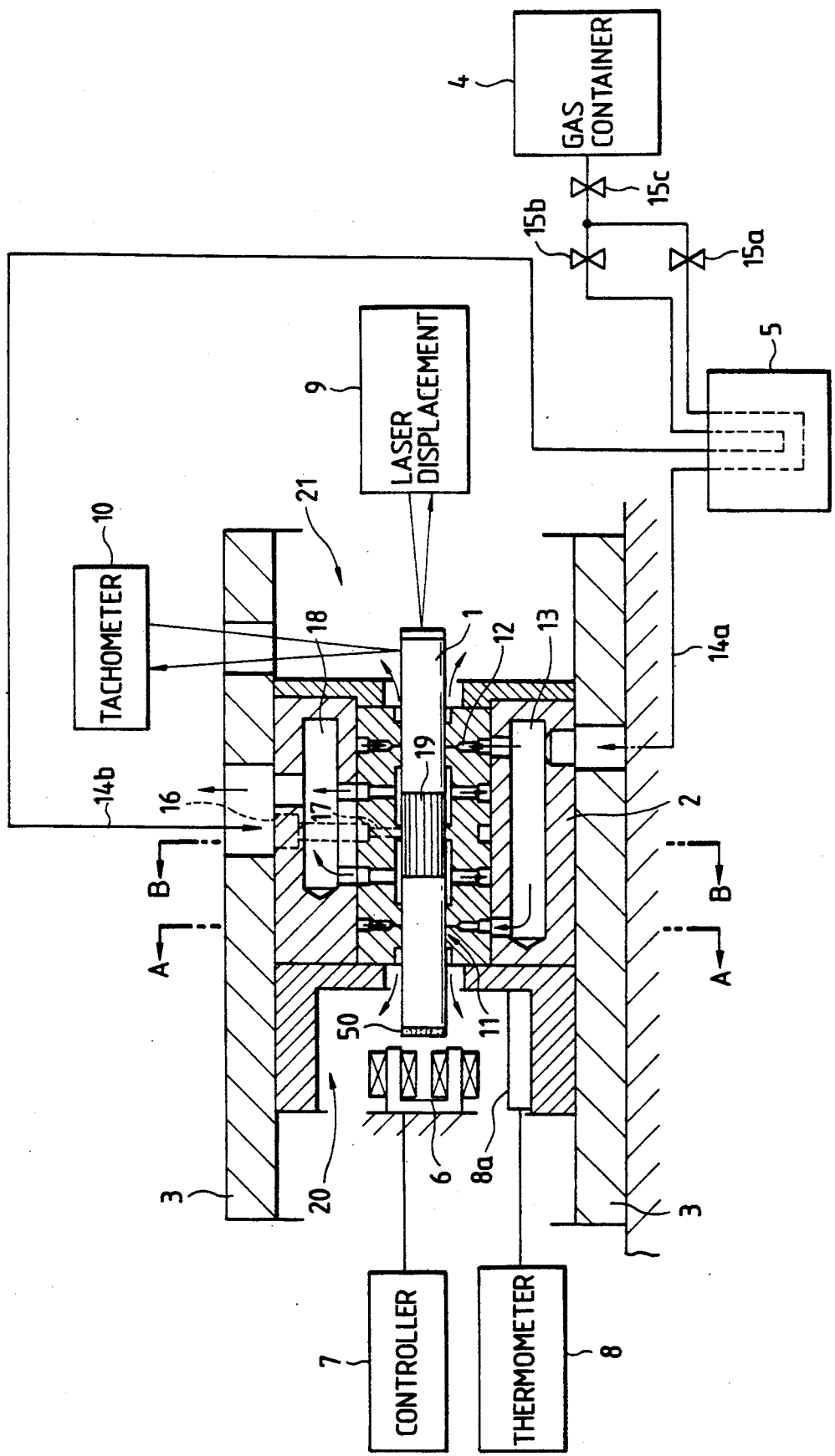
FIG. 1 is a longitudinal sectional view showing the arrangement of a device according to one embodiment of the present invention.
Figure 2:
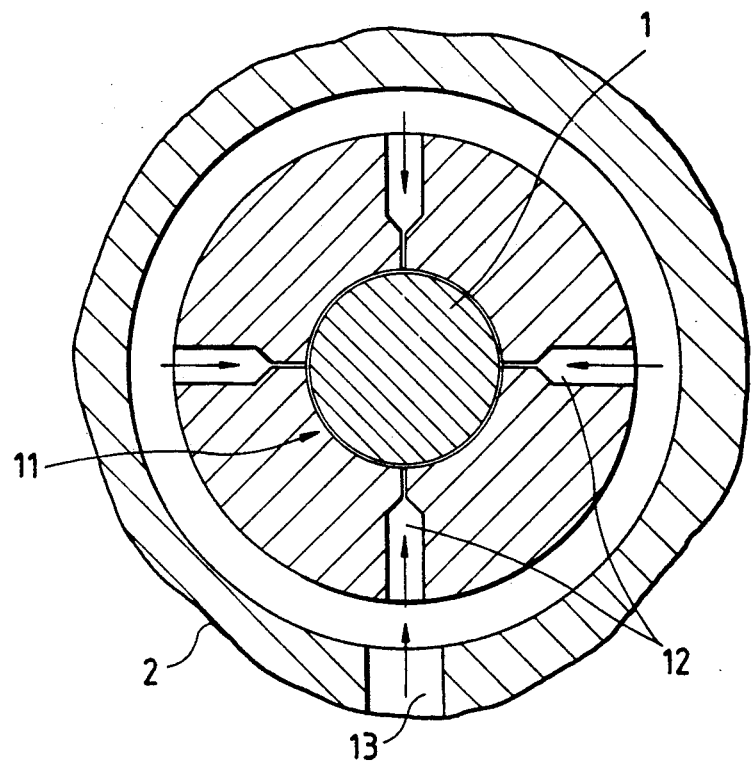
FIG. 2 is an enlarged sectional view taken along line A—A in FIG. 1.
Figure 3:
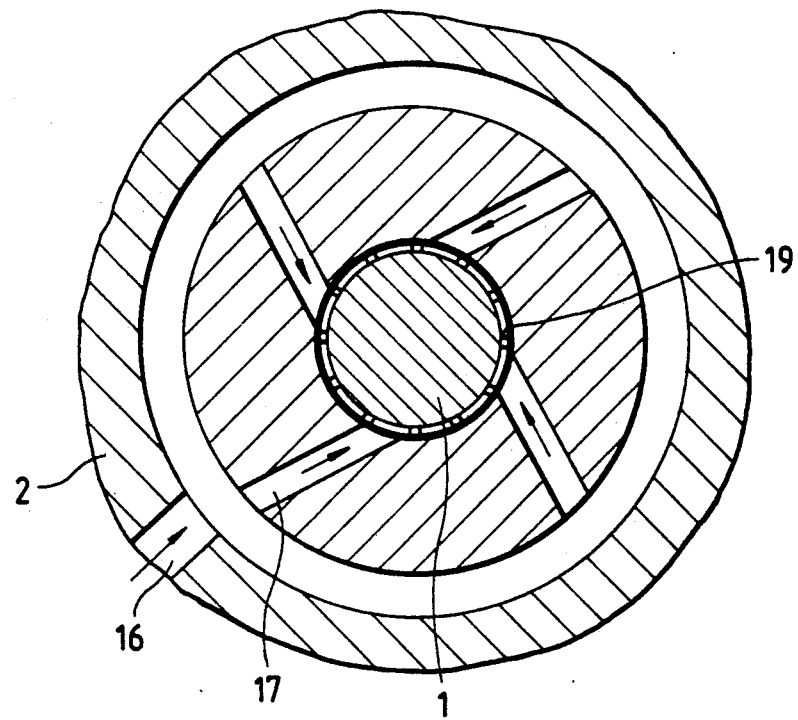
FIG. 3 is also an enlarged sectional view taken along line B—B in FIG. 1.

FIG. 1 is a longitudinal sectional view showing the arrangement of a superconductor characteristic measuring device according to one embodiment of the present invention. FIG. 2 is an enlarged sectional view taken along line A—A in FIG. 1. FIG. 3 is an enlarged sectional view taken along line B—B in FIG. 1.

As shown in those figures, the measuring device of the invention comprises: a specimen holding shaft 1 for holding a superconductor specimen 50 at its one end; a frame 2 supporting the shaft 1 horizontally: a heat insulating material 3 surrounding the frame 2; a container 4 keeping a temperature maintaining gas, namely, a helium gas; a cooling unit or heat exchanger 5 for cooling the helium gas with liquid nitrogen; an electromagnet 6 which is confronted with the superconductor specimen 50; a controller 7 for controlling the magnetic field strength of the electromagnet 6; a thermometer 8 for detecting the ambient temperature of the superconductor specimen 50 and the electromagnet 6 with a detector 8a; displacement detecting means, namely, a laser displacement gauge 9 for detecting the amount of axial displacement of the specimen holding shaft 1 in a non-contact mode; and rotational resistance detecting means, namely, an optical revolution counter or tachometer 10 for detecting the rotational resistance in a non-contact mode which acts on the specimen holding shaft 1.

The specimen holding shaft 1 is made of non-magnetic material, and the superconductor specimen is connected to the one end of the shaft 1 with adhesive.

The specimen holding shaft 1 penetrates the frame 1 horizontally. As shown in FIG. 2, a static pressure type gas bearing 11 is formed between the shaft 1 and the frame 2. The gas bearing 11 supports the specimen holding shaft 1 in such a manner that the shaft 1 is axially movable, and is rotatable. In FIG. 1, reference numeral 12 designates flow-out paths through which a bearing gas forming the gas bearing 11 flows out. Those flow-out paths 12 are connected through a lead-in path 13 to a pipe 14a for the cooling helium gas (hereinafter referred to as "a bearing pipe 14a", when applicable), which is provided outside the frame 2. Reference numeral 15a designates a valve connected to the bearing pipe 14a. The helium gas flowing into the gas bearing 11 is allowed to flow out through a lead-out path 18 and both open ends of the frame 1 while cooling the specimen holding shaft 1.

A lead-in path 16 for a shaft rotating gas, a jet path 17 and the lead-out path 18 are formed in the frame 2, and a turbine section 19 is formed at the middle of the specimen holding shaft 1. As shown in FIG. 3, the turbine section 19 and the jet paths 17 arranged around the turbine section 19 form means for rotating the specimen holding shaft 1 (hereinafter referred to as "a shaft rotating means", when applicable). The lead-in path 16 is connected to the other pipe 14b for the helium gas (hereinafter referred to as "a driving pipe 14b", when applicable). Further in FIG. 1, reference numeral 15b designates a valve connected to the driving pipe 14b; and 15c, a valve connected to the junction of the two pipes 14a and 14b.

The electromagnet 6 is fixedly installed at a predetermined position in one open end 20 (the left open end in FIG. 1) of the frame 2, and its magnetic field strength is controlled by the controller 7.

The laser displacement gauge 9 is provided on the side of the other open end of the frame 2, to apply a laser beam to the end of the specimen holding shaft 1 to measure the amount of displacement of the latter 1.

The optical revolution counter 10 is so positioned as to confront the exposed cylindrical wall of the specimen holding shaft 1.

A measurement with the measuring device thus constructed and the operation thereof will be described.

(1) Measurement of Repulsive Displacement

In measurement of the repulsive displacement of the superconductor specimen 50 with respect to the electromagnet 6, first the cooled helium gas is supplied to the gas bearing 11 only, and it is not supplied to the shaft rotating means, that is, the turbine section 19. Therefore, the specimen holding shaft 1 is supported in such a manner that it is not rotating but it is axially movable. The helium gas flows towards the electromagnet 6 while cooling the shaft 1. Therefore, the superconductor specimen 50 is cooled down to the critical temperature or lower by the shaft 1 thus cooled and the ambient atmosphere thus cooled.

On the other hand, the current applied to the electromagnet 6 is set to substantially zero so that no magnetic field is produced, and the specimen holding shaft 1 is moved towards the electromagnet 6 until the superconductor specimen 50 contacts the electromagnet 6; that is, the distance between the electromagnet and the superconductor specimen is set to zero (0) (at a standard position).

Under this condition, the value of the current applied to the electromagnet 6 is gradually increased. As a result, a repulsive force is generated between the magnetic field produced by the electromagnet 6 and the superconductor specimen 50, thus sliding the specimen holding shaft 1 away from the electromagnet 6. In this case, the magnetic flux of the electromagnet 6 scarcely penetrates the superconductor specimen 50.

In this operation, being supported horizontally by the gas bearing 11, the specimen holding shaft 1 is scarcely resisted by the frame 2. Since the magnetic field strength of the electromagnet 6 is gradually increased, the shaft 1 is slid at extremely low speed. Hence, the inertial force of the weight of the specimen holding shaft 1 does not act on the slide of the latter 1. That is, the superconductor specimen 50 and the specimen holding shaft 1 are moved away from the electromagnet 6 only by the repulsion of the specimen 50 against the electromagnet 6; and the distance between the electromagnet 6 and the superconductor specimen 50 is the repulsive displacement as it is.

The distance between the electromagnet 6 and the superconductor specimen 50; that is, the displacement of the specimen holding shaft 1 is measured by the laser displacement gauge 9.

The repulsive displacement of the superconductor specimen may be measured by relatively moving the superconductor specimen toward the magnet while the magnetic field of the magnet is constant.

Further, the following method of measurement may be conducted. That is, first, the magnetic force of the electromagnet 6 is kept at some value. The specimen holding shaft 1 is disposed to confront the electromagnet. A load is applied to one end of the specimen holding shaft 1 opposite to the superconductor specimen side so that the holding shaft 1 is moved toward the electromagnet 6 and stops at a predetermined position (standard position). The distance $h_0$ between the electromagnet 6 and the superconductive specimen 50 at that time is a standard distance. In this case, a part of the magnetic flux of the electromagnet 6 penetrates the superconductor specimen 50. Then the load is removed from the specimen holding shaft 1 at the position so that the specimen holding shaft is moved back due to the repulsive force to the superconductor specimen 1 against the electromagnet 6 and stops at some position. At that time, the distance $h_1$ between the electromagnet 6 and the superconductor specimen 50 is measured and the amount "$h_1-h_0$" is obtained. In this way, the amount of the repulsive displacement can be measured.

Further, in the above measuring methods, a cooled helium gas may be suppled to a gas rotation driving means, that is, the turbine section 19 so that the specimen holding shaft 1 is supported in such a manner that it is rotating and is axially movable.

In this state, at first, the current applied to the electromagnet 6 is set to substantially zero so that magnetic field is not generated. The specimen holding shaft 1 is moved to the electromagnet so that the superconductor specimen 50 contacts the electromagnet 6. That is, the distance between the electromagnet 6 and the superconductor specimen 50 is made zero (standard position).

From the above state, the electric current flown in the electromagnet 6 is gradually increased. Thus, the repulsive force between the magnetic field generated by the electromagnet 6 and the superconductor specimen 50 is increased so that the specimen holding shaft 1 slides away from the electromagnet 6 due to the repulsive force while it is rotating. In this case, the magnetic flux of the electromagnet 6 scarcely penetrates the superconductor 50. The distance between the position where the specimen holding shaft 1 stops and the standard position is measured by the laser displacement gauge 9 so that the repulsive force to the superconductor specimen under rotation can be measured.

Furthermore, the repulsive force to the superconductor specimen under rotation may be measured by at first keeping the magnetic force of the electromagnet 6 at some value, applying a load to a specimen holding shaft 1 under rotation to move it to the electromagnet 6, measuring the standard position where the shaft stops due to the balance between the repulsive force and the load, removing the load, and measuring the distance between the standard postion and the position where the superconductor specimen stops.

(2) Measurement of Rotational Resistance

Whether or not a type II superconductor is mixedly superconducting and normal-conducting, and the resistance when it is mixedly superconducting and normal-conducting, are measured as follows:

As was described above, under the condition that the superconductor specimen 50 and the electromagnet 6 repulse each other, the helium gas is supplied to the turbine section 19 to rotate the shaft 1 for a predetermined period of time, and then the supply of the gas is stopped.

If, in this case, the superconductor specimen 50 is of perfect diamagnetism, no rotational resistance acts on the superconductor specimen 50 and the specimen holding shaft 1, and therefore the shaft 1 is kept rotated for a long time. However, when the superconductor specimen 50 is in the above-described mixedly superconducting and normal-conducting state, then the flux pinning in the superconductor specimen 50 resists the rotation of the specimen holding shaft 1, so that the latter 1 will be stopped soon. Hence, the rotational resistance acting on the superconductor specimen 50 can be determined by measuring the period of time which elapses from the time instant that the rotating drive of the specimen holding shaft 1 is stopped until the shaft 1 stops by itself, and by calculating the time constant. The mixedly superconducting and normal-conducting range can be determined by changing the magnetic field condition.

Figure 4:
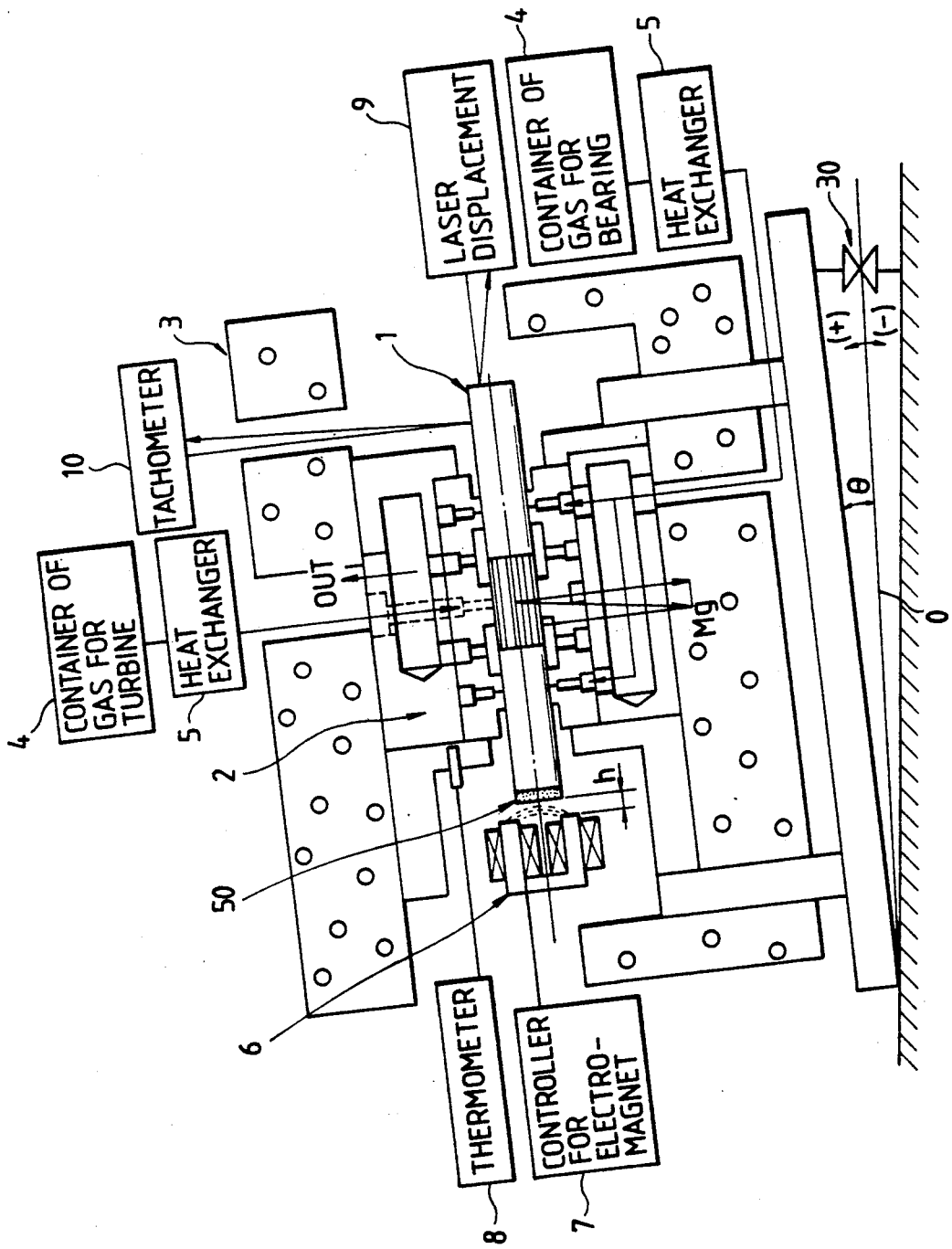
FIG. 4 is a sectional view showing a device for measuring characteristics of a superconductor under a load according to another embodiment of the pressing invention.

FIG. 4 is a sectional view showing a device for measuring characteristics of a superconductor under a load according to another embodiment of the present invention, in which a lift 30 as a load applying means is provided.

The entire of the device is mounted on an obliquely inclined base (downward at the right in FIG. 4). The lift 30 is provided between the base and the frame 2 (and the heat insulating material 3).

The lift 30 is, for example, a hydraulic cylinder, by which the entire of the device is inclined up and down (+ and − direction in FIG. 4) with respect to the horizontal line 0 as one end thereof is a fulcrum. By inclining the entire of the device so as to incline the specimen holding shaft 1 with respect to the horizontal line 0, the load F (mg sin $\theta$) is applied to the superconductor specimen 50 in a non-contact mode. Where, m is the mass of the specimen holding shaft 1 and the superconductor specimen 50, g is gravitational acceleration, and $\theta$ is an angle between the specimen holding shaft 1 and the horizontal line 0.

When the specimen holding shaft 1 is kept in the horizontal posture, the load F is 0 gf. When the inclination angle $\theta$ beteen the specimen holding shaft 1 and the horizontal line is set to the + direction, the superconductor specimen 50 is applied by the load directed toward the electromagnet 6. When the inclination angle $\theta$ is set to the − direction, the superconductor specimen 50 is applied by the load directed away from the electromagnet 6.

Accordingly, according to this embodiment, the above described measurements for the repulsive force and the rotational resistance of the superconductor specimen can be made under the condition in which the load is applied to the superconductor specimen.

That is, in the above described measuring methods, measurement under the condition in which the constant load F is applied to the superconductor specimen 50 can be conducted. That is, the repulsive force of the superconductor specimen under the load can be measured. Further, measurement can be made under the condition in which the superconductor specimen is rotating and is applied by the constant load F. That is, the repulsive force to the superconductor specimen 50 under the rotation and the load, can be measured. Furthermore, the rotational resistance due to the magnetic flux pinning in the superconductor specimen 50 can be measured under the condition in which the constant load is applied to the specimen. That is, the rotational resistance of the superconductor specimen under the load can be measured.

Figure 5:
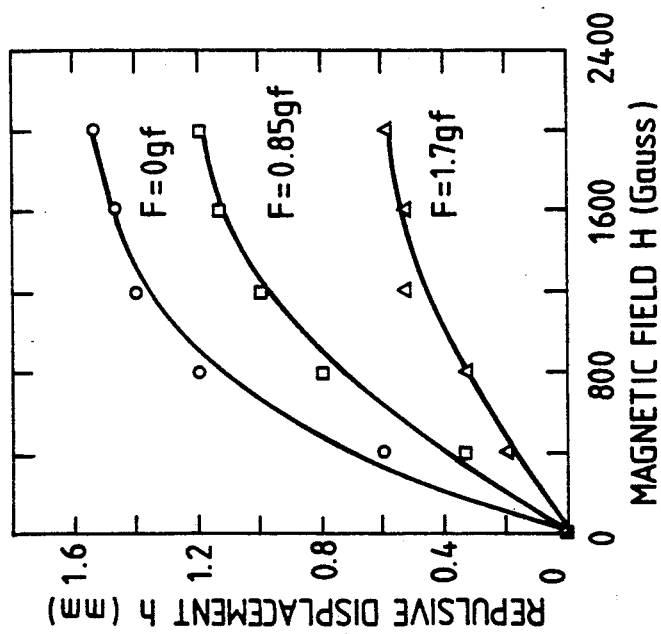
FIG. 5 is a graph showing the relation between a magnetic field and a repulsive displacement, which is obtained using the device of FIG. 4.

FIG. 5 shows experimental data of the repulsive displacement h of the superconductor specimen 50 with respect to the magnetic force H. The superconductor of $Y_1 Ba_2 Cu_3 O_{7-x}$ was used in the experiment. The load was 0 gf, 0.85 gf and 1.7 gf.

As is apparent from FIG. 5, the repulsive displacement under no load is largest. As the load increases, the repulsive displacement becomes small.

When the inclination angle $\theta$ between the specimen holding shaft 1 and the horizontal line 0 is set to the + direction, the degree of the Meisner effect of the superconductor specimen 50 against the load can be measured. When the inclination angle $\theta$ is set to the − direction, the degree of the suspension effect of the superconductor specimen 50 against the load can be measured.

In the measurement with respect to the magnetic flux pinning in the superconductor specimen under the load, when the load is large, the amount of the magnetic flux pinning in the specimen is large and the resistance is large. When the load is small, the amount of the magnetic flux pinning in the specimen is small and the resistance is small.

In the above embodiment, the lift 30 is exemplified as the load applying means. However, the load applying means may be an apparatus for applying wind pressure to one end of the specimen holding shaft 1.

Figure 7:
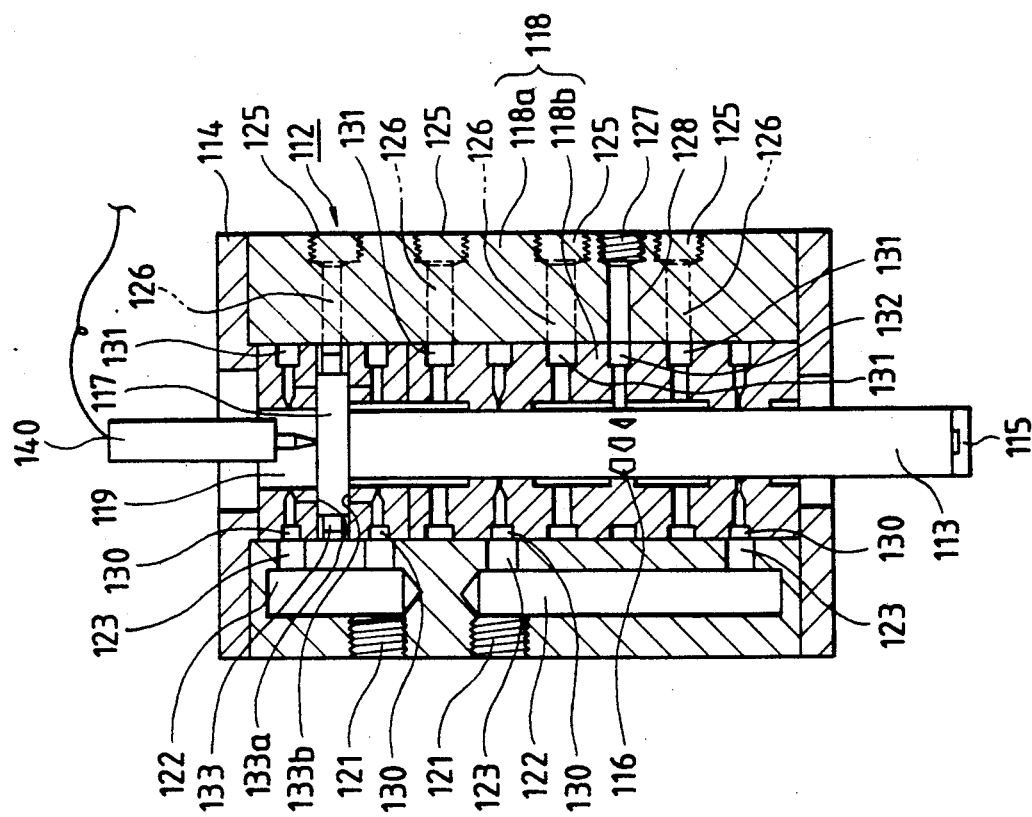
FIG. 7 is an enlarged sectional view showing a part of the measuring device of FIG. 6.
Figure 6:
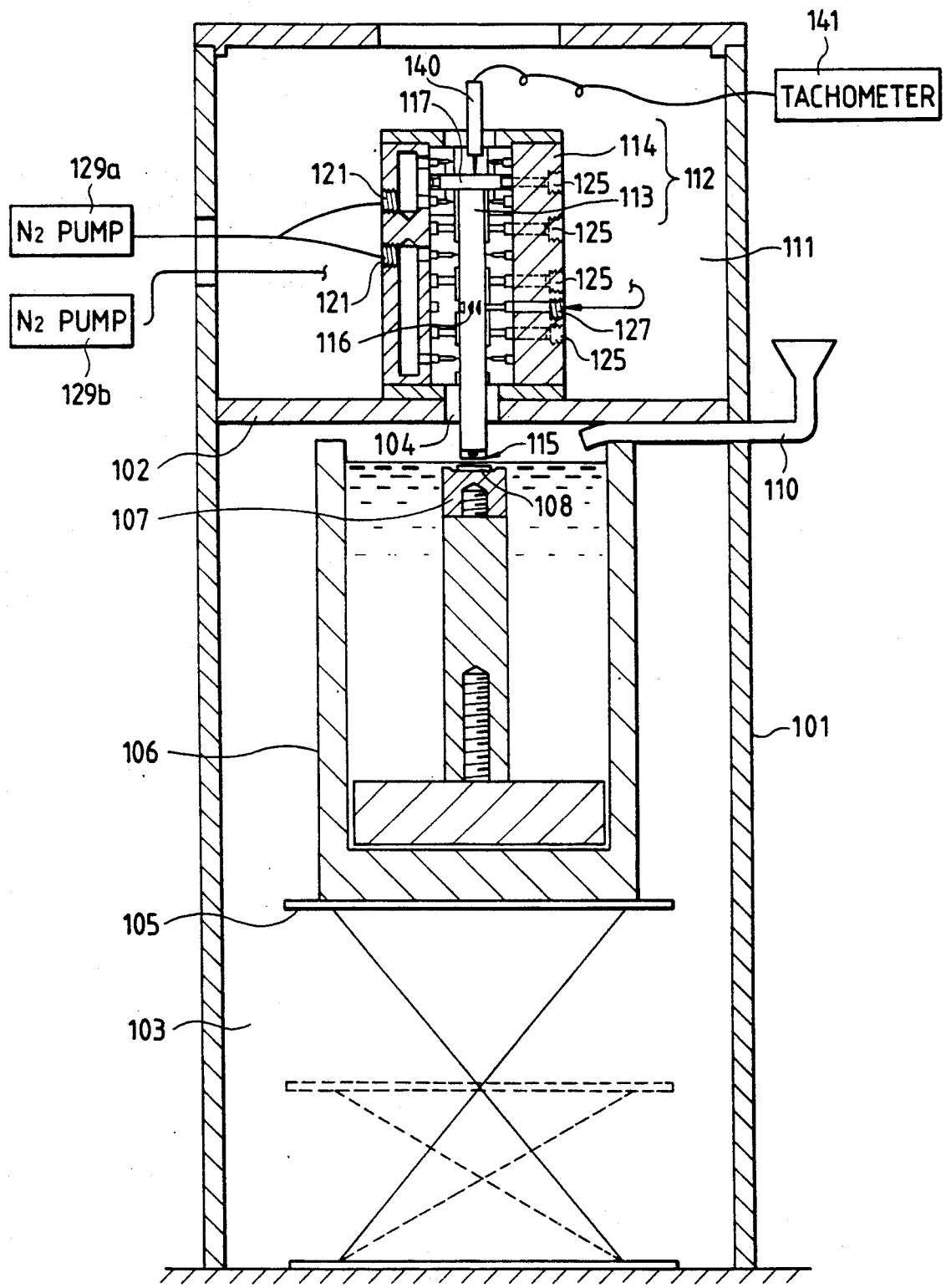
FIG. 6 is a sectional view showing a superconductor characteristic measuring device according to still another embodiment of the present invention.

FIG. 6 is a longitudinal sectional view of a superconductor characteristic measuring device according to still another embodiment of the present invention. FIG. 7 is an enlarged sectional view showing a part of the measuring device.

In FIGS. 6 and 7, reference numeral 101 designates a housing with an open bottom, the housing being made of an acrylic plate or the like. The housing 101 is divided by a partition board 102 into the upper chamber 111 and the lower chamber 103. In the lower chamber 103, a height adjusting lift 105 is provided, and cooling means, namely, a cooling vessel 106 is placed on the height adjusting lift 105. And a specimen holder 107 (or first holding means) is provided in the cooling vessel 106 in such a manner that it is protruded from the center of the bottom of the cooling vessel. A recess is formed at the top end of the specimen holder 107. A superconductor specimen 108 is placed in the recess thus formed, in such a manner that it is confronted with an opening 104 formed at the center of the partition board 102. A liquid nitrogen lead-in pipe 110 is provided to supply a liquid nitrogen into the cooling vessel 106 from a container provided outside the housing 101.

A magnet rotor 112 is mounted on the partition board 102 in the upper chamber 111. The magnet rotor 112 is made up of a spindle 113 (or second holding means) extended vertically, and a static pressure support mechanism (or supporting means) which supports the spindle 113 in a non-contact mode. The spindle 113 is made of non-magnetic material. A permanent magnet 115 is bonded to the lower end of the spindle with adhesive. A turbine section 106 is formed in the middle of the spindle 113. A disk 117 larger in diameter than the spindle 113 is secured to the upper end of the latter 113. A mark for detecting an amount of rotation is provided on the upper surface of the disk 117 at such a position as is shifted from the center of the upper surface.

The static pressure support mechanism 114 comprises a pivoting hole 119 formed in a frame 118, to pivotally support the spindle 113. The frame 118 consists of an outer frame 118a and an inner frame 118b. Two bearing nitrogen gas inlets 121 are formed in the upper portion and in the middle portion of the outer frame 118a, respectively. Two lead-in base flow-paths 122 are formed in the outer frame 118a in such a manner that they are communicated with the inlets 121, respectively. Furthermore, connecting flow-paths 123 are formed in the outer frame 118a in such a manner that they are extended from the lead-in base flow-paths 122 to the inner frame 118b. First, second, third and fourth bearing nitrogen gas outlets 125 are formed in the outer wall of the outer frame 118a in such a manner that they are arranged vertically in the stated order from above and are located at positions circumferentially different from those of the above-described gas paths. Connecting flow-paths 126 are extended from the outlets 125 to the inner frame 118b. A turbine driving nitrogen gas inlet 127 is formed in the outer wall of the outer frame 118 in such a manner that it is located at a position different from those of the outlets 125 and between the third and fourth outlets 125. A connecting flow-path 128 is extended from the inlet 127 to the inner frame 118b. A nitrogen gas pump 129a is connected to the inlets 121, and another nitrogen gas 129b is connected to the inlet 127. The pump 129b forms a rotation driving mechanism (or rotation driving means).

Bearing nitrogen gas lead-in paths 130 connected to the connecting flow-paths 123 in the outer frame 118a are formed in the inner frame 118b. Furthermore, bearing nitrogen gas lead-out paths 131 connected to the connecting flow-paths 126, and a driving nitrogen gas lead-in path 132 connected to the connecting flow-path 128 are formed in the inner frame 118b. An annular recess 133 is formed in the inner frame 118b in such a manner that it confronts the uppermost lead-out path 131, so that the disk 117 of the spindle 113 is loosely fitted in the annular recess 133. The lead-in paths 130 located above and below the annular recess 133 are communicated to the annular recess 133 respectively through upward surface 133b and downward surface 133a thereof. As the spindle 113 is set as described above, the lead-in path 128 is confronted with the turbine section 116, and the lower end portion of the spindle 113 is passed through the central opening 104 of the partition board 102 so that the permanent magnet 115 on the lower end of the spindle is confronted with the superconductor specimen 108.

Further in FIGS. 6 and 7, reference numeral 140 designates a reflected-light sensor penetrating the static pressure support mechanism 114 from above in such a manner that its lower end meets the mark on the disk 117 as the spindle 113 rotates. The reflected-light sensor 140 is connected to a revolution counter 141. The reflected-light sensor 140 and the revolution counter 141 form an amount-of-rotation detecting means (or amount-of-rotation detecting means).

The magnet rotor 112 is constructed as described above. That is, it provides a non-contact type static pressure bearing structure including the spindle 113 and the inner frame 118b in it. When the pump 129a is operated to supply a nitrogen gas through the nitrogen gas lead-in path 130 into the pivoting hole 119, the fluid film formed between the inner cylindrical wall of the inner frame 118 and the cylindrical wall of the spindle 113 by the nitrogen gas supplied through the lead-in paths 130 communicated with the lower lead-in base flow-path 122 supports the spindle 113 radially in such a manner that it is not in contact with the inner cylindrical wall of the inner frame 118. When the nitrogen gas is supplied through the lead-in paths 130, the fluid film formed between the upper and lower surfaces of the disk 117 and the upward and downward surfaces 133b and 133a of the annular recess 133 supports the spindle 113 axially in such a manner that the spindle is not in contact with the inner cylindrical wall of the inner frame 118b.

An operation of measuring an amount of rotation in relation to rotational resistance through above-described measuring device will be described.

Under the condition that the pump 129a is in operation, the other pump 129b is operated to jet the nitrogen gas to the turbine section 116 thereby to rotate the spindle 113 for a predetermined period of time, and then the driving of the turbine section 116 is suspended.

If, in this case, the superconductor specimen 108 is perfectly diamagnetic, no rotational resistance acts on the superconductor specimen 108 and the spindle 113, and the spindle 113 will rotate continuously. However, if the superconductor specimen 108 is mixedly superconducting and normal-conducting as was described above, the rotation of the spindle 113 is resisted by the magnetic flux pinning in the superconductor specimen 108, and therefore the spindle is stopped in a short period of time. The revolution counter 141 counts the detection signals which the reflected-light sensor 140 outputs when detecting the mark on the disk 117 for the period of time which elapses from the driving of the turbine section is suspended until the spindle 113 stops by itself; that is, the amount of rotation of the spindle until the latter stops, is detected. The amount of rotation thus detected is utilized to calculate a time constant. According to the time constant thus calculated, the rotational resistance acting on the superconductor specimen 8 can be determined. That is, when the time constant is large, the rotational resistance is low; and when it is small, the rotational resistance is high. In addition, the mixedly superconducting and normal-conducting range in relation to the rotational resistance can be detected.

In the above-described embodiment, the superconductor specimen is held stationary, and the magnet is rotated. It goes without saying that the superconductor specimen may be rotated with the magnet held stationary. In the latter case, the magnet may be an electromagnet.

The non-contact bearing structure may be of a magnetic bearing.

Furthermore, the amount-of-rotation detecting means may be such that the period of time is detected which elapses from the time instant that the driving of rotation of the spindle is suspended until the rotation of the spindle stops.

As described above, according to the present invention, characteristics of a superconductor such as the repulsive force of the superconductor against a magnet can be measured with ease and with high accuracy.

That is, according to the first aspect of the invention, the superconductor specimen and the specimen holding shaft are supported by the supporting means. Therefore, the repulsive force can be directly detected independently of the weight of the specimen and the shaft; that is, the repulsive displacement can be measured accurately.

According to the second aspect of the invention, the superconductor specimen and the specimen holding shaft are forcibly rotated, and the rotational resistance is measured, whereby the mixedly superconducting and normal conducting range, and the mechanical resistance attributing to the flux pinning in the superconductor can be measured.

According to the third aspect of the invention, with only one measuring device, the repulsive displacement can be measured under any load and at any speed of rotation, and the range in which the superconductor is mixedly superconducting and normal-conducting, and the mechanical resistance can be measured. Furthermore, as the temperature maintaining gas is used to support and rotate the specimen holding shaft, the means for supporting and rotating the specimen holding shaft and the means for cooling the superconductor specimen can be simplified as much, which contributes to miniaturization of the measuring device.

Further, according to the embodiment shown in FIGS. 6 and 7, by detecting the amount of rotation of the first or second holding means, the rotational resistance and the mixedly superconducting and normal-conducting range of the type II superconductor with respect to a magnet can be detected with ease. Furthermore, the static pressure support mechanism supports the spindle both radially and axially, and therefore the rotation is carried out smoothly, and the amount of rotation of the spindle can be detected with high accuracy. In addition, the spindle with the magnet on its lower end is held vertically, and the specimen holder and the cooling unit are provided below the spindle. Therefore, the measuring device is extended vertical, and is compact.

What is claimed is:

1. A method of measuring repulsive displacement of a superconductor, comprising the steps of:
   supporting said superconductor in a predetermined position without contact inhibiting the repulsive displacement;
   disposing a magnet at a position opposed to said superconductor along an axis of displacement;
   increasing the magnetic forced of said magnet; and
   measuring a repulsive displacement of said superconductor from said predetermined position to a stop position.

2. A method of measuring repulsive displacement of a superconductor, comprising the steps of:
   supporting said superconductor without contact inhibiting the repulsive displacement;
   disposing a magnet at a position opposed to said superconductor along an axis of the displacement;
   moving said superconductor toward said magnet under a predetermined load to determine a standard position;
   releasing said load; and
   measuring the repulsive displacement of said superconductor from said standard position to a stop position.

3. A method of measuring repulsive displacement of a superconductor, comprising the steps of:
   supporting said superconductor in a predetermined position without contact inhibiting the repulsive displacement;
   disposing a magnet at a position opposed to said superconductor along an axis of the displacement;
   placing a constant load along the axis on said superconductor;
   increasing the magnetic force of said magnet; and
   measuring the repulsive displacement of said superconductor from said predetermined position to a stop position.

4. A method of measuring repulsive displacement of a superconductor, comprising the steps of:
   supporting said superconductor without contact inhibiting the repulsive displacement;
   disposing a magnet at a position opposed to said superconductor along an axis of the displacement;
   placing a constant first load along the axis on said superconductor;
   relatively moving said superconductor toward said magnet under a second load to determine a standard position;
   releasing said second load; and
   measuring the repulsive displacement of said superconductor from said standard position to a stop position.

5. A method of measuring repulsive displacement of a superconductor, comprising the steps of:
   supporting said superconductor without contact at a predetermined position so that said superconductor is axially and rotatably movable;
   disposing a magnet at a position axially opposed to said superconductor;
   relatively rotating said superconductor at a constant speed with respect to said magnet;
   increasing the magnetic force of said magnet; and
   measuring the repulsive displacement of said superconductor from said standard position to a stop position.

6. A method of measuring repulsive displacement of a superconductor, comprising the steps of:
   supporting said superconductor without contact so that said superconductor is axially and rotatably movable;
   disposing a magnet means at a position axially opposed to said superconductor;
   relatively rotating said superconductor at a constant speed with respect to said magnet;
   relatively moving said superconductor toward said magnet under a load to determine a standard position;
   releasing said load; and
   measuring the repulsive displacement of said superconductor from said standard position to a stop position.

7. A method of measuring repulsive displacement of a superconductor, comprising the steps of:
   supporting said superconductor without contact at a predetermined position so that said superconductor is axially and rotatably movable;
   disposing a magnet means at a position axially opposed to said superconductor;
   placing a constant axial load on said superconductor;
   relatively rotating said superconductor at a constant speed with respect to said magnet;
   increasing the magnetic force of said magnet;
   measuring the repulsive displacement of said superconductor from said predetermined position to a stop position.

8. A method of measuring repulsive displacement of a superconductor, comprising the steps of:
   supporting said superconductor without contact so that said superconductor is axially and rotatably movable;
   disposing a magnet means at a position axially opposed to said superconductor;
   placing a constant first axial load on said superconductor;
   relatively rotating said superconductor at a constant speed with respect to said magnet;
   relatively moving said superconductor toward said magnet under a second load to determine a standard position;
   releasing said second load; and
   measuring the repulsive displacement of said superconductor from said standard position to a stop position.

9. A method of measuring a rotational resistance due to flux-pinning in a superconductor, comprising the steps of:
   supporting said superconductor without contact so that said superconductor is axially and rotatably movable;
   disposing a magnet means at a position axially opposed to said superconductor;
   relatively rotating said superconductor with respect to said magnet by a rotating drive force;
   releasing said rotating drive force; and
   measuring a period of time until the rotation stops.

10. A method of measuring a rotational resistance due to flux-pinning in a superconductor, comprising the steps of:

supporting said superconductor without contact so that said superconductor is axially and rotatably movable;

disposing a magnet at a position axially opposed to said superconductor;

relatively rotating said superconductor with respect to said magnet by a rotating drive force;

placing a constant axial load on said superconductor;

releasing said rotating drive force; and measuring a period of time until the rotation stops.

11. A device for measuring characteristics of a superconductor, comprising:

a specimen holding member for holding a superconductor specimen;

supporting means for supporting said specimen holding member without direct contact with the structure of the supporting means in such a manner that said specimen holding member is movable in a horizontal direction;

a magnet positioned in such a manner as to confront, in the horizontal direction, said superconductor specimen held by said specimen holding member; and displacement detecting means for detecting, in a non-contact mode, an amount of displacement of said specimen holding member in the horizontal direction.

12. A device as claimed in claim 11, further comprising inclining means for inclining said supporting means with respect to the horizontal line.

13. A device for measuring characteristics of a superconductor, comprising:

a specimen holding shaft for holding a superconductor specimen;

a magnet positioned in such a manner as to confront said superconductor specimen held by said specimen holding shaft;

supporting means for supporting said specimen holding shaft to rotate and move toward and away from said magnet without direct contact with the structure of the supporting means;

driving means for rotating said superconductor specimen; and rotational resistance detecting means for detecting a rotational resistance of said superconductor specimen.

14. A device for measuring characteristics of a superconductor, comprising:

a specimen holding shaft for holding a superconductor specimen;

a gas bearing for supporting said specimen holding shaft in such a manner that said specimen holding shaft is held horizontally and is rotatable and axially movable;

gas drive means for jetting a gas to a turbine section provided on said specimen holding shaft, to rotate said specimen holding shaft;

gas supplying means for supplying a temperature maintaining gas to said gas drive means and said gas bearing;

an electromagnet positioned in such a manner as to confront said specimen in a horizontal direction;

displacement detecting means for detecting an amount of axial displacement of said specimen holding shaft; and rotational resistance detecting means for detecting a rotational resistance of said superconductor specimen.

15. A device for measuring characteristics of a superconductor, comprising:

first holding means for holding a superconductor specimen;

second holding means for holding a magnet in such a manner that such magnet confronts said superconductor specimen;

supporting means for rotatably supporting without contact with the structure of the supporting means said first or second holding means in the axis of rotation which coincides with the direction in which said superconductor specimen and said magnet confront each other;

rotating means for rotating said first or second holding means; and amount of rotation detecting means for detecting the amount of rotation of said first or second holding means which is rotated by said rotating means.

16. A device as claimed in claim 12, wherein said second holding means is a spindle extended vertically and having a magnet on the lower end thereof, said supporting means is a static pressure support mechanism for supporting said spindle radially and axially in a non-contact mode, said rotating means is a rotating mechanism provided for said spindle, said amount-of-rotation detecting means is an amount-of-rotation detecting mechanism provided for said spindle, said first holding means is a specimen holder for holding said superconductor specimen in such a manner that said superconductor specimen is confronted with said magnet, and a cooling unit for cooling said superconductor specimen is provided.

* * * * *

UNITED STATES PATENT AND TRADEMARK OFFICE
CERTIFICATE OF CORRECTION

PATENT NO.  : 5,111,140
DATED       : May 05, 1992
INVENTOR(S) : Ryoichi TAKAHATA It is certified that error appears in the above-identified patent and that said Letters Patent is hereby corrected as shown below:

Claim 1, column 13, line 15, change "forced" to --force--.

Signed and Sealed this

Twenty-eighth Day of September, 1993

Attest:

BRUCE LEHMAN

Attesting Officer

Commissioner of Patents and Trademarks